United States Patent [19]

Morritt et al.

[11] Patent Number: 4,648,386
[45] Date of Patent: Mar. 10, 1987

[54] LASER BRONCHOSCOPE VENTILATOR

[76] Inventors: Graham N. Morritt, 16 Westfield Drive; Malvolio L. Paes, 18 Roseworth Crescent, both of Gosforth, Newcastle-on-Tyne, Tyne and Wear; Ian D. Conacher, 44 Moorside South, Fenham, Newcastle-on-Tyne, Tyne and Wear; John R. Gutridge, 20 Hertford Avenue, East Sheen, London SW14 8 EE; Timothy R. Snellgrove, 4 Oakbank, Prestwich, Manchester, all of England

[21] Appl. No.: 652,061

[22] Filed: Sep. 19, 1984

[30] Foreign Application Priority Data

Jan. 28, 1984 [GB] United Kingdom ................. 8402313

[51] Int. Cl.$^4$ .......................... A61B 1/26; A61B 17/36
[52] U.S. Cl. .................... 128/4; 128/303.15; 128/204.25; 604/21; 604/26; 604/35
[58] Field of Search .......................... 128/4, 5, 6, 8, 10, 128/11, 303.15, 303.1, 205.23, 204.25, 395, 396, 397, 398; 641/21, 26, 35

[56] References Cited

U.S. PATENT DOCUMENTS

| 3,414,896 | 12/1968 | Glick et al. | 128/205.23 |
| 3,906,953 | 9/1975 | Wallace et al. | 128/303.1 |
| 3,941,120 | 3/1976 | Lee | 128/4 |
| 4,316,182 | 2/1982 | Hodgson | 128/205.23 |
| 4,402,310 | 9/1983 | Kimura | 128/4 |
| 4,422,457 | 12/1983 | Hattori | 128/303.15 |
| 4,538,604 | 9/1985 | Usry et al. | 128/204.25 |
| 4,565,194 | 1/1986 | Weerda et al. | 128/204.25 |

Primary Examiner—Henry J. Recla
Attorney, Agent, or Firm—Brady, O'Boyle & Gates

[57] ABSTRACT

Bronchoscopy apparatus comprises a tubular bronchoscope instrument having a laser manipulator at its proximal or rear end. A gas passage element running along the length of the bronchoscope is connected via a control system to pressurized oxygen and a source of reduced pressure (suction). The control system is operable to switch between a simple ventilation mode and a suction mode. The suction mode may be prolonged to give adequate time for laser surgery. An audible alarm is activated shortly before suction is discontinued and pressurized oxygen is applied.

6 Claims, 2 Drawing Figures

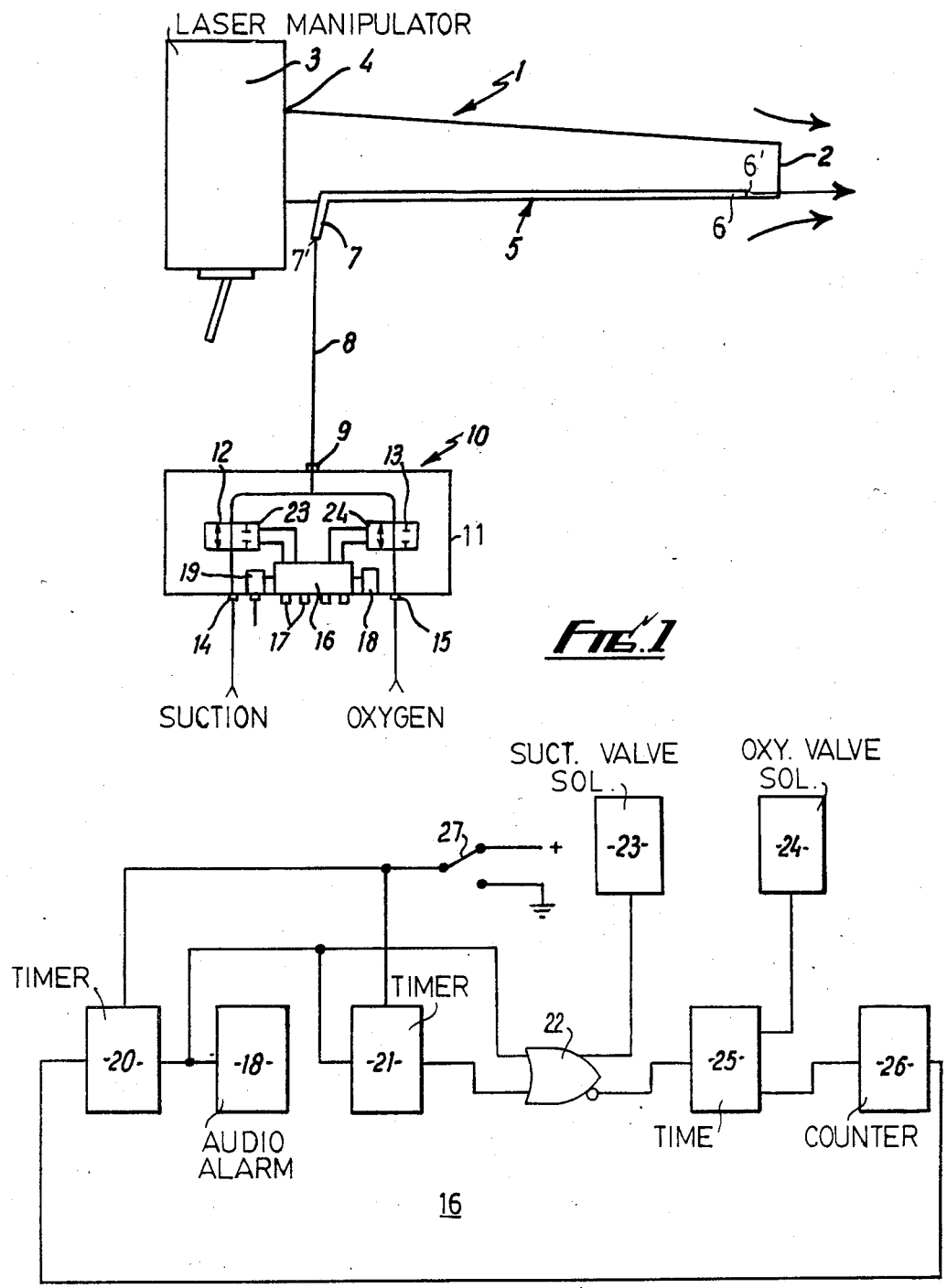

LASER BRONCHOSCOPE VENTILATOR

BACKGROUND OF THE INVENTION

This invention relates to bronchoscopy and is more particularly concerned with a ventilation system for use with a viewing bronchoscope.

A bronchoscope comprises a tubular instrument which can be inserted down a patient's trachea to permit viewing of the bronchi and to aid in the performance of certain bronchial surgical procedures. It is common practice to use an open-ended bronchoscope tube and to ventilate the patient during bronchoscopy by means of a short venturi needle located at the open proximal end of the tube, often attached to the rim of the opening. A high pressure gas stream (oxygen) is directed down the tube from the venturi needle and this entrains a large volume of air which is drawn through the open proximal end thereby ensuring adequate ventilation.

However, it is now known to mount a laser manipulator at the proximal end of the bronchoscope tube and, with this arrangement, the problem arises that inflow of entrained air is blocked and thereby ventilation is reduced. Also, on use of the laser manipulator, smoke is generated and this becomes deposited in the patient's lungs if ventilation is effected during application of the laser. In the latter respect, it is known to use a bronchoscope having a separate suction channel for evacuation of smoke but there is the problem of synchronising ventilation and suction with smoke generation.

SUMMARY

An objet of the present invention is to overcome or at least appreciably reduce the above-identified problems.

According to one aspect of the present invention therefore there is provided bronchoscopy apparatus comprising a tubular bronchoscope instrument having a forward, open end and a rear or proximal end, a relatively narrow elongated passage or conduit associated with said instrument and adapted for directing gas flow longitudinally of said instrument between an outlet port at or adjacent said forward end and an input port at or adjacent said rear end, and a ventilation system connected to said passage end portion and switchable between a first state in which high pressure gas is arranged to be fed to said passage and a second state in which said feed of high pressure gas is discontinued.

With this arrangement adequate patient ventilation can be achieved even when the proximal end of the tubular instrument is blocked in so far as a high pressure gas jet can be expelled from the forward end of the instrument thereby acting to entrain a relatively large volume of air around the outside of the tube at said end.

Moreover, in the case where the apparatus incorporates a laser manipulator or other smoke-generating surgical implement, there is the possibility of ensuring that smoke generation is effected solely or largely whilst the ventilation system is in the said second state and ventilation is arrested.

In the said second state the passage may be closed or opened freely to the atmosphere, corresponding to a simple ventilation mode of the system. Alternatively, and especially in the case of smoke generation, the system may have a suction mode whereby the passage is arranged to be connected to a source of reduced pressure or suction in the said second state. The ventilation system may be adjustable so that the mode can be preselected in accordance with either of the abovementioned alternatives.

Most preferably the ventilation system is arranged to switch automatically from one to the other of the said states after respective predetermined periods of time. This switching is implemented by an electronic control circuit connected to solenoid valves or the like and provision is made for preselection of the duration at one or both of the respective time periods.

In a particularly preferred embodiment, and in the case where the ventilation system can operate selectively either in the simple ventilation mode or in the suction mode, provision is made for automatic switching between these modes after predetermined (and possibly pre-adjustable) numbers of cycles of operation in each mode. Thus, for example, the system may operate in the simple ventilation mode for say 1 to 10 cycles and then in the suction mode for a single cycle.

The time period for the said second state may be appreciably longer than the time period for the first state, especially when the ventilation system is in the suction mode, to give adequate time e.g. for performance of laser manipulation. Moreover, a device is provided which operates at or shortly before the end of the time period for the second state to give warning of the imminent switch over to the ventilation phase. Suitably such warning device may comprise an audible alarm or the like.

Thus, and in accordance with a second aspect of the present invention there is provided a ventilation system, for use with bronchoscopy apparatus of the kind described above, comprising first and second gas connectors respectively for sources of reduced and increased pressure, a third gas connector for connection to said apparatus, a valve arrangement operable to link said first and second connectors selectively with said third connector, a control circuit for controlling operation of said valve arrangement so as to effect linking of said first and second connectors to said third connector for respective predetermined periods of time, and a warning device arranged to produce an alarm output at or close to the end of each period of time during which said first connector is linked to said third connector.

BRIEF DESCRIPTION OF THE DRAWING

The invention will now be described further by way of example only and with reference to the accompanying drawing in which:

FIG. 1 is a diagrammatic view of one form of bronchoscopy apparatus according to the invention; and FIG. 2 is a circuit diagram of a control circuit of the apparatus.

DESCRIPTION OF THE PREFERRED EMBODIMENT

The apparatus comprises a bronchoscope tube 1 (e.g. of the kind known as a Wolf bronchoscope) having a freely open forward end 2. A laser manipulator 3 (e.g. a Sharplan laser manipulator, a device well known in the art) is fixed across and blocks the proximal or rear end 4 of the tube 1.

A narrow passage or conduit 5 runs along the inside of the tube 1 and terminates at one end 6 in an output port 6' a short distance away from the open end 2 of the tube 1. At the other end, the passage 5 has a terminal input portion 7 including an input port 7' which projects externally of the tube 1 close to the laser manipulator 3.

The passage 5 may comprise a piece of tubing of relatively narrow cross section, a pipe or needle attached to the inner wall surface of tube 1 or may be formed integrally therewith.

The input portion 7 is connected (e.g. by a length of flexible piping 8) to a connector 9 on a ventilation system control unit 10. This unit contains, within a housing 11, an arrangement of solenoid-operated control valves 12, 13 interposed between the connector 9 and two further connectors 15 and 14 adapted for connection respectively to a source of high pressure gas (e.g. an oxygen cylinder providing oxygen at 60 psi) and a source of reduced pressure (suction apparatus), not shown. The housed unit 10 further contains an electronic control circuit 16 the details of which are shown in FIG. 2, arranged to control operation of the solenoid valves 12, 13 and connected to manual controls 17 mounted on the unit and an audible warning device 18. A mains-powered low voltage d.c. (e.g. 15 v d.c.) power supply 19 is provided.

The control circuit 16, as shown in FIG. 2 comprises a variable timer 20 which produces an output after a predetermined time (which is preset with one of the manual controls 17) within a typical range of 13 to 50 seconds. The timer 20 is connected to the alarm device 18 and to a second timer 21 which produces an output after a predetermined period of time, for example, 5 seconds. Both timers 20, 21 are connected to a OR/-NOR logic gate 22 which is connected in turn to the suction valve solenoid 23 (via a relay, not shown) and a third timer 25 which has on and off periods which are individually adjustable with respective said manual controls 17. Operation of the timer 25 is inhibited and the solenoid 23 is actuated when either of the timers 20 and 21 is switched on. Conversely the solenoid 23 is deactuated and the timer 25 is switched on when both timers 20 and 21 are switched off. The timer 25 is connected to the oxygen valve solenoid 24 (via a relay, not shown) and to a decade counter 26 which is arranged to produce an output which resets the timer 20 after a predetermined count which is preset within the range 1 to 10 with one of the manual controls 17. A switch 27 is provided to override the timers 20, 21 when the switch contacts are connected to ground, otherwise a positive (+) supply is applied for powering the timers 20, 21.

In use, when the switch 27 is not set to override the timers 20, 21, the timer 25 initially operates to switch on and off with a pre-adjusted duty cycle. The oxygen solenoid 24 is correspondingly switched on and off and pressurised oxygen is alternately connected to and disconnected from the passage 5 in the bronchoscope. Whenever pressurised oxygen is connected to the passage 5 it is expelled from the end 6' of the passage 5 and flows through the open forward end 2 of the bronchoscope 1 entraining relatively large volumes of air drawn along the outer side of the tube 1. Adequate ventilation of the patient is therefore achieved.

After a predetermined number of cycles of the timer 25, corresponding to the maximum pre-adjusted count of the counter 26, the timer 20 is triggered. This causes the timer 21 (and hence the solenoid 24) to switch off and the solenoid 23 to switch on, via the gate 22. Surgical procedures can now be carried out with the laser manipulator and any smoke produced is drawn from the patient's lungs.

After a predetermined period of time determined by the timer 20 the alarm 18 is triggered and the timer 21 is initiated. During the five-second period of operation of the timer 21 an output is fed to the gate 22 to hold the solenoid 23 and timer 25 respectively in their actuated and deactuated states. The surgeon is alerted by the audible alarm and has the opportunity of arresting surgical procedures during the five-second period.

At the end of the five-second period the solenoid 23 is deactuated, the timer 25 is actuated and the above-described cycle is repeated.

If suction is not required, the switch 27 is operated to override the timers 20, 21 and the timer 25 then operates to switch the solenoid 24 on and off continuously.

It is of course to be understood that the invention is not intended to be restricted to the details of the above embodiment which are described by way of example only.

Accordingly all modifications, alterations, and changes coming within the spirit and scope of the invention as set forth in the following claims are meant to be included.

We claim:

1. Laser bronchoscopy apparatus for use in performing bronchial surgical procedures on a patient comprising:

a tubular bronchoscope instrument including a body portion having a forward end and a rear end;

a laser manipulator secured to and blocking said rear end of said instrument;

a gas passage (means) tube of relatively small cross section extending along the body portion of said instrument for a major portion of its length and having an outlet port in the region of said forward end of said instrument and an input port in the region of said rear end of said instrument, said tube extending along a side surface of the body portion so as to leave said body portion free for direction of said laser manipulator therealong;

a ventilation system, including first and second control valves, connected to said input port, said ventilation system further being respectively connected from a pressurized source of gas and a source of reduced pressure or suction to said input port by said first and second control values;

control means having first and second operational modes for controlling the opening and closing of said first and second valves and being switchable between a first or ventilation mode and a second or suction mode;

said ventilation mode effecting alternate opening and closing of said first valve while maintaining said second valve closed to cause pressurized gas to flow intermittently along said gas passage tube from said input port to said outlet port for ventilating said patient, and said suction mode effecting opening of said second valve while maintaining said first valve closed to cause suction to be applied to said gas passage tube from said input port to said outlet port for removing smoke while surgical procedures are performed with said laser manipulator on said patient;

said control means being further operable to switch automatically from said first mode to said second mode after a predetermined number of cycles of alternate opening and closing of said first valve and to switch automatically from said second mode to said first mode after a predetermined period of time in said second mode.

2. The apparatus according to claim 1 wherein said control means includes an alarm device which operates at or shortly before the end of said predetermined period of time to produce an audible warning.

3. The apparatus according to claim 1 wherein said pressurised gas comprises oxygen.

4. The apparatus according to claim 1 wherein said gas passage tube comprises an elongated tubular member whose cross section is small in relation to the cross section of said body portion.

5. The apparatus according to claim 4 wherein said elongated tubular member is located along the inner wall surface of said body portion of the bronchoscope instrument.

6. Ventilating laser bronchoscopy apparatus for use in performing bronchial surgical procedures on a patient comprising:

a tubular bronchoscope instrument having a forward end and a rear end and wherein said forward end is open;

a laser manipulator secured to and blocking said rear end of said instrument;

an elongated tubular gas conduit of relatively small cross section extending along a substantial portion of the length of said instrument and having at one end thereof an outlet port in the region of said forward end of said instrument and an input port at the opposite end thereof in the region of said rear end of said instrument, said tubular conduit further being positioned along an inside surface of said instrument so as to leave said instrument free for direction of said laser manipulator therealong;

a ventilating system connected to said input port, said system further comprising first and second control valves respectively connected to a source of high suction;

a control device for controlling opening and closing of said valves and being switchable between a first or ventilation mode and a second or suction mode, (modes,) said control device being operable in said first mode to effect alternate operning and closing of said first valve while said second valve is closed to thereby cause said high pressure gas to flow intermittently along said gas conduit from said input port to said outlet port for ventilating said patient, said control device being operable in said second mode to effect opening of said second valve while said first valve is closed to thereby cause suction to be applied to said gas conduit for removing smoke while surgical procedurs are performed with said laser manipulator on said patient;

said control device being further operable to switch automatically from said first mode to said second mode after a predetermined number of cycles of alternate opening and closing of said first valve and to switch automatically from said second mode to said first mode after a predetermined period of time in said second mode; and an alarm device which operates at or shortly before the end of said predetermined period of time to produce an audible warning of the end of said second mode.

* * * * *